United States Patent
Prevrhal et al.

(10) Patent No.: US 9,082,211 B2
(45) Date of Patent: Jul. 14, 2015

(54) MEASUREMENT OF BLOOD FLOW DYNAMICS WITH X-RAY COMPUTED TOMOGRAPHY: DYNAMIC CT ANGIOGRAPHY

(75) Inventors: Sven Prevrhal, San Francisco, CA (US); Jean Rinkel, Oakland, CA (US); Carlos Forsythe, Sebastopol, CA (US); Benjamin M. Yeh, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1260 days.

(21) Appl. No.: 12/806,212

(22) Filed: May 6, 2010

(65) Prior Publication Data

US 2011/0274333 A1    Nov. 10, 2011

(51) Int. Cl.
| | |
|---|---|
| G06K 9/00 | (2006.01) |
| G06T 11/00 | (2006.01) |
| A61B 6/03 | (2006.01) |
| A61B 6/00 | (2006.01) |

(52) U.S. Cl.
CPC ............. *G06T 11/005* (2013.01); *A61B 6/032* (2013.01); *A61B 6/481* (2013.01); *A61B 6/504* (2013.01); *G06T 2211/404* (2013.01); *G06T 2211/412* (2013.01)

(58) Field of Classification Search
CPC ......... G06T 7/0012; A61B 8/06; A61B 5/055
USPC ....................................... 382/128–131; 378/4
See application file for complete search history.

(56) References Cited

U.S. PATENT DOCUMENTS

| | | | |
|---|---|---|---|
| 2006/0140336 A1* | 6/2006 | Russinger et al. ................. | 378/4 |
| 2006/0159326 A1* | 7/2006 | Rasche et al. ................. | 382/131 |
| 2009/0078875 A1* | 3/2009 | Rousso et al. ........... | 250/363.04 |
| 2011/0228897 A1* | 9/2011 | Kobayashi ........................ | 378/8 |

FOREIGN PATENT DOCUMENTS

DE      4220282 A1      12/1993

OTHER PUBLICATIONS

Acevedo-Bolton, Gabriel et al., "Estimating the Hemodynamic Impact of Interventional Treatments of Aneurysms: Numerical Simulation with Experimental Validation: Technical Case Report," Neurosurgery, Aug. 2006, vol. 59, No. 2, E429-30.

Berg, Marja, et al., "Multi-Detector Row CT Angiography in the Assessment of Carotid Artery Disease in Symptomatic Patients: Comparison with Rotational Angiography and Digital Subtraction Angiography," May 2005, American Journal of Neuroradiology, vol. 26, issue 5, pp. 1022-1034.

Hittmair, Karl et al., "Accuracy of Predicting and Controlling Time-Dependent Aortic Enhancement from a Test Bolus Injection," Mar.-Apr. 2001, Journal of Computer Assisted Tomography, vol. 25, No. 2, pp. 287-394.

(Continued)

*Primary Examiner* — Luke Gilligan
(74) *Attorney, Agent, or Firm* — Kilpatrick Townsend & Stockton LLP

(57) ABSTRACT

In various embodiments, systems and methods can provide accurate measurements of blood flow dynamics in a subject. Projection data acquired during a computed tomography (CT) scan of the subject can be used to determine information representing inflow of a contrast material. Accordingly, a measurement of flow velocity, in addition to other aspects of flow, may be obtained from the projection data.

31 Claims, 11 Drawing Sheets

(56) References Cited

OTHER PUBLICATIONS

Levin, David C. et al., "The Effect of the Introduction of MR and CT Angiography on the Utilization of Catheter Angiography for Peripheral Arterial Disease," Journal of the American College of Radiology, Jul. 2007, vol. 4, No. 7, pp. 457-460.

Minino, Arialdi M. et al., "Deaths: Injuries, 2002," National Vital Statistics Reports, Centers for Disease Control and Prevention, Jan. 31, 2006, vol. 54, No. 10, pp. 1-125.

Mwipatayi, Bibombe Patrice et al., "Balloon angioplasty compared with stenting for treatment of femoropopliteal occlusive disease: A meta-analysis," Journal of Vascular Surgery, Feb. 2008, vol. 47, issue 2, pp. 461-469.

Prevrhal, S. et al. "Measuring blood flow speed in CT raw data," European Congress of Radiology 2008, Mar. 7-11, 2008, Vienna, Austria (2 pages).

Prevrhal, Sven et al., "CT Angiographic Measurement of Vascular Blood Flow Velocity by Using Projection Data," Radiology, Dec. 2011, vol. 261, No. 3, pp. 923-929.

Weiss, Clifford R. et al., "Ct Pulmonary Angiography is the First-Line Imaging Test for Acute Pulmonary Embolism: A Survey of US Clinicians," Academic Radiology, Apr. 2006, vol. 13, issue 4, pp. 434-446.

\* cited by examiner

MEASUREMENT OF BLOOD FLOW DYNAMICS WITH X-RAY COMPUTED TOMOGRAPHY: DYNAMIC CT ANGIOGRAPHY

BACKGROUND OF THE INVENTION

Arterial disease can be considered one of the leading causes of mortality and morbidity in the United States, responsible for every third death or 2,500 deaths per day in the U.S. alone. Arterial disease may claims more lives each year than cancer, chronic lower respiratory diseases, accidents, and diabetes mellitus combined. As a result, clinical angiographic imaging (CAI) to diagnose vascular disease has increased by approximately 23% over the past 5 years. CAI may now be performed for approximately 1% of all Medicare patients.

Computed-Tomography Angiography (CTA) is one noninvasive imaging modality for evaluation of blood vessels and may be steadily replacing conventional invasive catheter-based angiography as the first-line diagnostic test for the evaluation of arterial disease. CTA can virtually replace all other alternative imaging modalities for some indications. CTA offers many advantages for the evaluation of arterial disease, including ease of use, excellent patient tolerance, rapid image acquisition, and outstanding morphological assessment of arterial stenoses, plaque, and mural irregularities.

However, one limitation of CTA is that CTA provides little to no information regarding the physiology of blood flow in a subject, such as flow velocity and turbulence. The absence of such blood flow data can lead to ambiguity regarding the functional relevance of the morphological findings provided by CTA. Furthermore, such ambiguity may result in a misinterpretation of the severity of arterial stenoses. Other available imaging methods that allow for blood flow assessments can also be limited because these methods either impose a relatively high risk of injury to the patient (e.g., conventional invasive catheter angiography) or are simply limited in scope (e.g., ultrasound). Furthermore, data obtained from exams that provide anatomical information can be difficult to combine with data obtain from exams that provide physiological information.

Accordingly, what is desired is to solve problems relating to using CTA and other imaging methods for the evaluation of arterial disease, some of which may be discussed herein. Additionally, what is desired is to reduce drawbacks using CTA for the evaluation of arterial disease, some of which may be discussed herein.

BRIEF SUMMARY OF THE INVENTION

In various embodiments, data collected from medical imaging devices may be used to determine blood flow dynamics, such as velocity, volume, pressure, etc. In one example, X-ray computed tomography (CT) can provide cross-sectional images of an area of interest, such as a series of two-dimensional X-ray images taken around a single axis of rotation. Various processing techniques can be used to analyze raw CT data to compute one or more three-dimensional images of the area of interest from the cross-sectional images providing measurements of blood flow dynamics in a subject.

In at least one embodiment, a method performed by an information processing device is provided for determining blood flow dynamics in a subject. The information processing device receives projection data indicative of a temporal change associated with flow of a contrast medium in a subject. Based on the projection data, the information processing device determines a contrast concentration at each of a plurality of projection angles. Blood flow velocity, volume, pressure, or the like, in the subject is determined by the information processing device based on comparing the contrast concentration at each of the plurality of projection angles across two or more rows of the multi-row CT scanner. The information processing device can generate information associated with blood flow dynamics of the subject for use in diagnostics and treatment, both in real-time and offline.

Determining a contrast concentration at each of the plurality of projection angles may include pre-processing of the projection data. For example, a portion of the projection data representing data acquired before inflow of the contrast material may be used as a reference to filter backgrounds or the like. A contrast-only sinusoidal trace may be generated in response to subtracting a reference sinogram acquired before inflow of the contrast medium from one or more sinograms acquired during inflow of the contrast medium at least one of the plurality of projection angles.

In some embodiments, a maximum grey value may be determined at each of the plurality of projection angles. Comparing the contrast concentration at each of the plurality of projection angles across one or more rows of a multi-row CT scanner may include determining a correlation between the contrast concentration at each projection angle and at least one of the rows. A square difference of the contrast concentration of a first row and of the contrast concentration of a second row may then be calculated.

In further embodiments, information associated with blood flow dynamics may be generated, logged, reported, or displayed on a display device. A set of images may be generated depicting a portion of anatomy of a subject that was the focus of one or more CT scans and a visual representation of information associated with blood flow dynamics.

Various systems, apparatuses, methods, computer-readable storage media, may be provided that include techniques of measuring blood flow dynamics as discussed herein.

A further understanding of the nature, advantages, and improvements offered by those innovations disclosed herein may be realized by reference to remaining portions of this disclosure and any accompanying drawings.

BRIEF DESCRIPTION OF THE DRAWINGS

In order to better describe and illustrate embodiments and/or examples of any innovations presented within this disclosure, reference may be made to one or more accompanying drawings. The additional details or examples used to describe the one or more accompanying drawings should not be considered as limitations to the scope of any of the disclosed inventions, any of the presently described embodiments and/or examples, or the presently understood best mode of any innovations presented within this disclosure.

DETAILED DESCRIPTION OF THE INVENTION

Angiography is generally used as a medical test to help physicians or other medical and clinical personnel diagnose and treat medical conditions related to blood vessels. Angiography may use one or more imaging technologies to produce images of blood vessels. In some cases, a contrast material may be injected into a subject in order to produce pictures of blood vessels throughout the body. Angiography may be performed using X-rays with invasive catheters, or using more non-invasive techniques, such as computed tomography (CT), magnetic resonance imaging (MRI), or the like. In general, an ideal imaging method for vascular evaluation would be noninvasive, well tolerated, fast, and deliver excellent anatomical and physiological information about the blood vessels.

Figure 1:
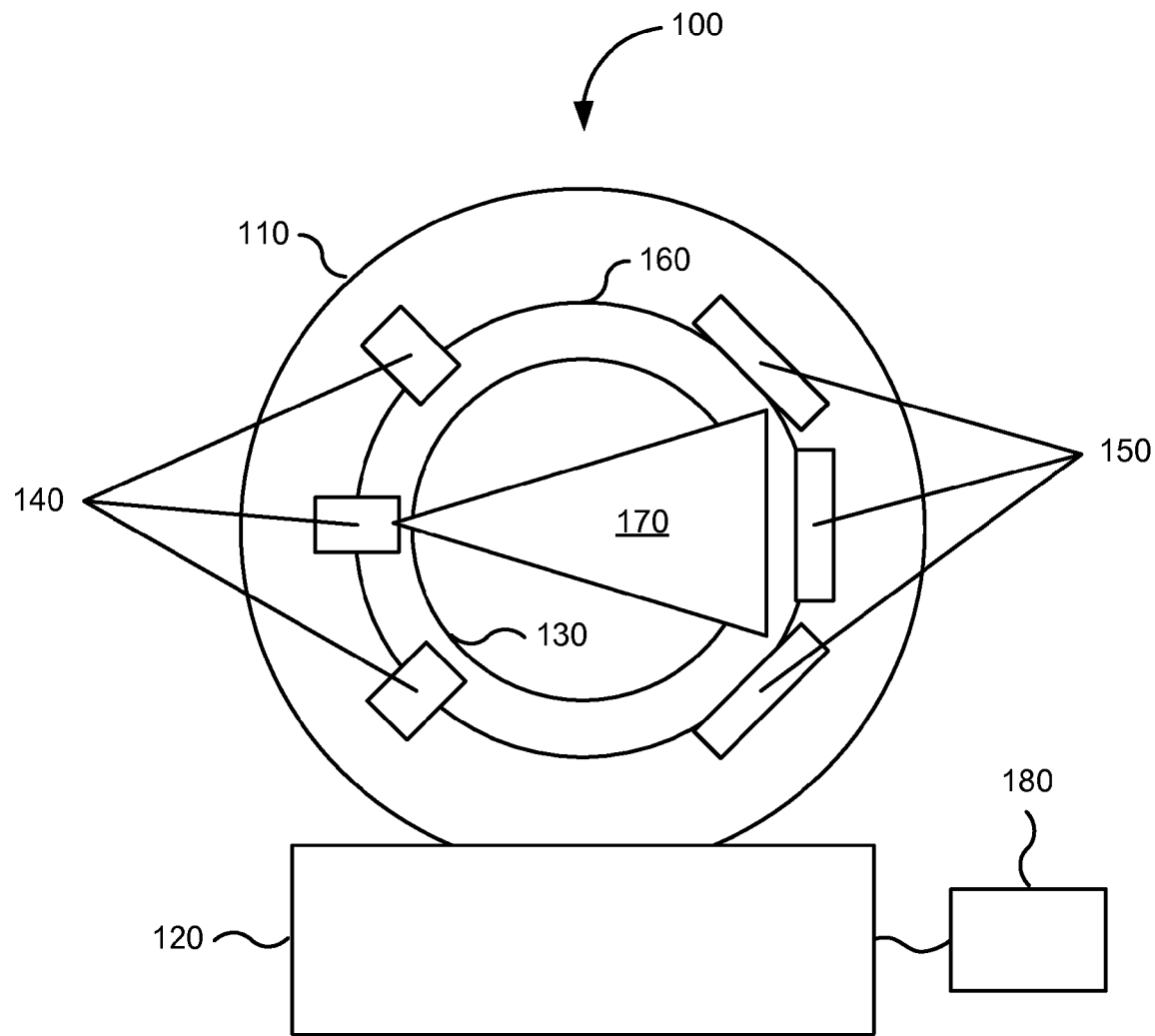
FIG. 1 is an illustration of a medical imaging device that may be used in various embodiments according to the present invention for the measurement of blood flow dynamics.

FIG. 1 is an illustration of medical imaging device 100 that may be used in various embodiments according to the present invention for the measurement of blood flow dynamics. In general, medical imaging device 100 can include any device that provides internal or external images of a subject, such as computed tomography (CT) devices, magnetic resonance imaging (MRI) device, or the like. In this example, medical imaging device 100 is embodied as a CT scanner that includes torus 110 that is supported by base 120. Center opening 130 can be formed in torus 110 and be configured to receive all or part of a subject. Center opening 130 may receive patient anatomy, which is to be scanned when medical imaging device 100 is used for applications, such as CTA or the like.

Torus 110 can include hardware and/or software elements configured to scan all or part of a subject placed in or substantially within center opening 130. For example, torus 110 may include one or more X-ray generator assemblies 140 and one or more X-ray detector assemblies 150. In one arrangement, X-ray generator assemblies 140 and X-ray detector assemblies 150 may be mounted to assembly 160 in diametrically opposing relation, such that one or more X-ray beams 170 (generated by X-ray generator assemblies 140 and detected by X-ray detector assemblies 150) are passed through all or part of patient anatomy disposed in or substantially within center opening 130. At least one of X-ray generator assemblies 140 and at least one of X-ray detector assemblies 150 may be positioned opposite each other in a linear array on assembly 160.

In some embodiments, an array may be mounted to assembly 160 of more than one of X-ray generator assemblies 140 and more than one X-ray detector assemblies 150. Such an array may be used to permit medical imaging device 100 to acquire multiple simultaneous scans of all or part of the subject. These multiple simultaneous scans may be called slices or sections. Medical imaging device 100 may further acquire multiple slices or sections simultaneously using different settings, profiles, imaging rates, or the like. Medical imaging device 100 may also include features known and used in typical medical imaging devices, such as conventional and helical CT scanners, as well was multidetector CT (MDCT), also know as multidetector-row computed tomography, multidetector-row CT, multisection CT, multislice computed tomography, and multislice CT. In various embodiments, assembly 160 may be configured to rotate around all or part of a subject to be scanned. For example, X-ray generator assemblies 140 and X-ray detector assemblies 150 can be mounted on assembly 160 so that they may be rotated concentrically about center opening 130. X-ray beams 170 therefore can be passed through patient anatomy along a full range of radial positions.

Various electronic hardware and/or software elements may be included for controlling the operation of medical imaging device 100. For example, base 120 may include hardware and/or software elements configured to control or otherwise operate components of a scan, such as X-ray generator assemblies 140, X-ray detector assemblies 150, and assembly 160. In some embodiments, torus 110 and base 120 may include hardware and/or software elements configured to process scan data. In other embodiments, medical imaging device 100 can be coupled to information processing device 180. Information processing device 180 may be configured to receive scan data and process the scan data according to techniques disclosed herein. Information processing device 180 may be located in torus 110, base 120, or otherwise communicatively coupled to medical imaging device 100 as shown in FIG. 1. Some examples of information processing device 180 can include computing devices or logic machines having a processor (e.g., a programmable processing unit) and memory (e.g., a computer-readable storage medium), personal computers (PCs), workstations, mainframes, application-specific devices, embedded devices, and associated operating systems, applications, drivers, or the like.

As discussed above, medical imaging device 100 may be used with X-ray computed tomography (CT) which provides a radiological imaging method employing tomography, a process of three-dimensional imaging by consecutive sections or sectioning. In X-ray CT, beams of X-rays are passed through a volume of interest from one or more different angles to produce CT data that represents cross-sectional images of the area of interest, such as a series of two-dimensional X-ray images taken around a single axis of rotation. Therefore, X-ray CT may produce a volume of digital CT data. Various processing techniques can be used to analyze the volume of CT data to compute one or more three-dimensional images of the area of interest from the cross-sectional images. Thus, these images can be assembled into a three-dimensional picture of the area being studied.

The CT images may be computed from the CT data in the axial or transverse plane of a body (e.g., orthogonal to the axis of rotation which typically coincides with the long axis of the body) and may be reformatted in various planes or even as volumetric (3D) representations of structures. Some processing techniques (e.g., such as windowing) used can demonstrate various structures inside the body based on the structures ability to attenuate or block an X-ray beam.

Figure 2:
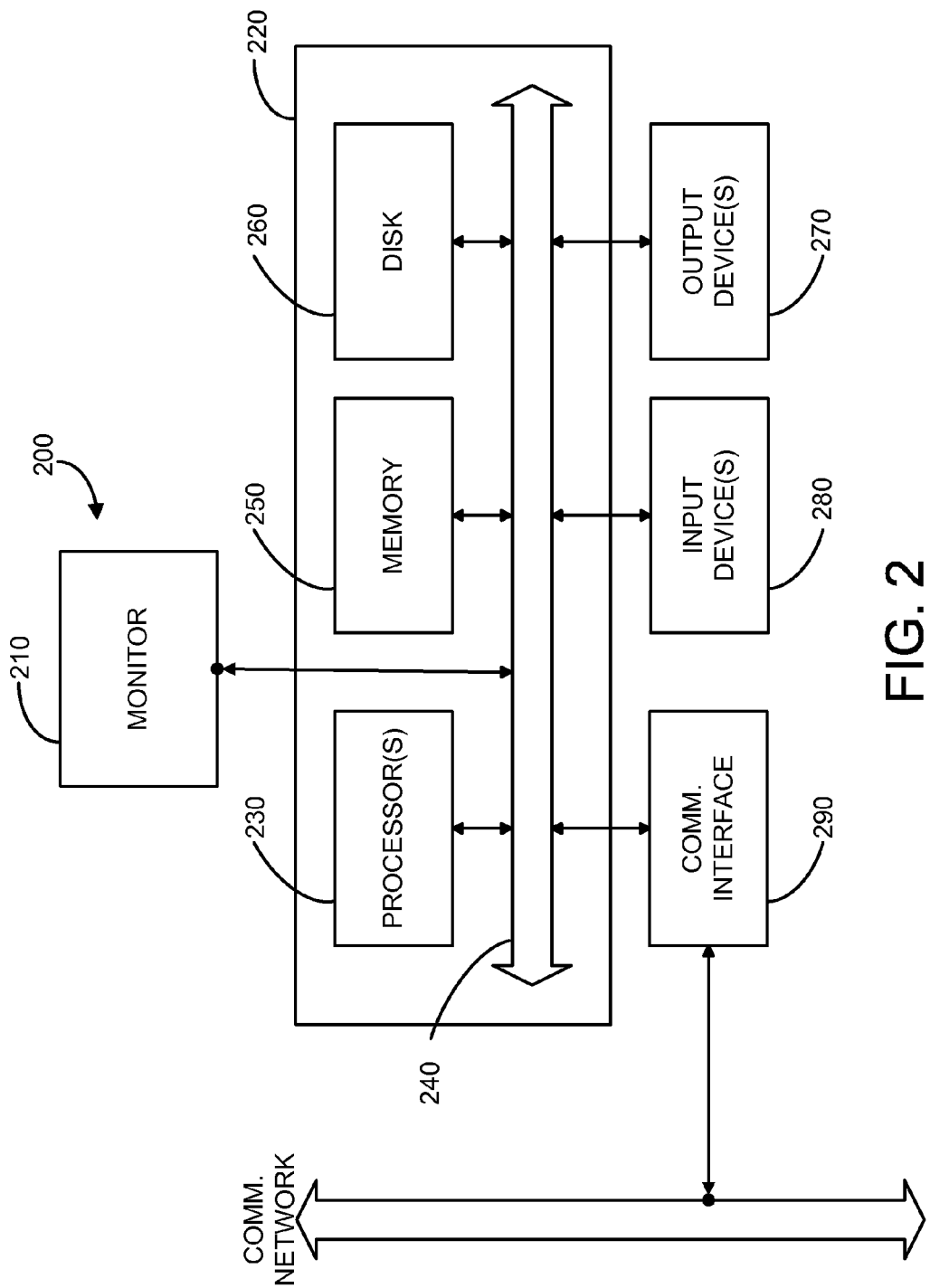
FIG. 2 is a block diagram of a computer system or information processing device that may be used with the medical imaging device of FIG. 1 for the measurement of blood flow dynamics in various embodiments according to the present invention.

FIG. 2 is a block diagram of computer system or information processing device 200 that may be used with medical imaging device 100 of FIG. 1 for the measurement of blood flow dynamics in various embodiments according to the present invention. For example, information processing device 180 of FIG. 1 may be embodied as computer system 200.

FIG. 2 is merely illustrative of a general-purpose computer system programmed according to techniques within this disclosure or a specific information processing device for an embodiment incorporating an invention whose teachings may be presented herein and does not limit the scope of the invention as recited in the claims. One of ordinary skill in the art would recognize other variations, modifications, and alternatives to computer system 200 that remain within the scope and equivalents of the disclosure.

In one embodiment, computer system 200 includes monitor 210, computer 220 (which includes processor(s) 230, bus subsystem 240, memory subsystem 250, and disk subsystem 260), user output devices 270, user input devices 280, and communications interface 290. Monitor 210 can include hardware and/or software elements configured to generate visual representations or displays of information. Some examples of monitor 210 may include familiar display devices, such as a television monitor, a cathode ray tube (CRT), a liquid crystal display (LCD), or the like. In some embodiments, monitor 210 may provide an input interface, such as incorporating touch screen technologies.

Computer 220 can include familiar computer components, such one or more central processing units (CPUs), memories or storage devices, graphics processing units (GPUs), communication systems, interface cards, or the like. As shown in FIG. 2, computer 220 may include one or more processor(s) 230 that communicate with a number of peripheral devices via bus subsystem 240. Processor(s) 230 may include commercially available central processing units or the like. Bus subsystem 240 can include mechanisms for letting the various components and subsystems of computer 220 communicate with each other as intended. Although bus subsystem 290 is shown schematically as a single bus, alternative embodiments of the bus subsystem may utilize multiple bus subsystems. Peripheral devices that communicate with processor(s) 230 may include memory subsystem 250, disk subsystem 260, user output devices 270, user input devices 280, communications interface 290, or the like.

Memory subsystem 250 and disk subsystem 260 are examples of physical storage media configured to store data. Memory subsystem 250 may include a number of memories including random access memory (RAM) for volatile storage of program code, instructions, and data during program execution and read only memory (ROM) in which fixed program code, instructions, and data are stored. Disk subsystem 260 may include a number of file storage systems providing persistent (non-volatile) storage for programs and data. Other types of physical storage media include floppy disks, removable hard disks, optical storage media such as CD-ROMS, DVDs and bar codes, semiconductor memories such as flash memories, read-only-memories (ROMS), battery-backed volatile memories, networked storage devices, or the like.

Memory subsystem 250 and disk subsystem 260 may be configured to store programming and data constructs that provide functionality or features of techniques discussed herein. Software code modules and/or processor instructions that when executed by processor(s) 230 implement or otherwise provide the functionality may be stored in memory subsystem 250 and disk subsystem 260.

User input devices 270 can include hardware and/or software elements configured to receive input from a user for processing by components of computer system 200. User input devices can include all possible types of devices and mechanisms for inputting information to computer system 220. These may include a keyboard, a keypad, a touch screen, a touch interface incorporated into a display, audio input devices such as microphones and voice recognition systems, and other types of input devices. In various embodiments, user input devices 270 can be embodied as a computer mouse, a trackball, a track pad, a joystick, a wireless remote, a drawing tablet, a voice command system, an eye tracking system, or the like. In some embodiments, user input devices 270 are configured to allow a user to select or otherwise interact with objects, icons, text, or the like that may appear on monitor 210 via a command, motions, or gestures, such as a click of a button or the like.

User output devices 280 can include hardware and/or software elements configured to output information to a user from components of computer system 200. User output devices can include all possible types of devices and mechanisms for outputting information from computer 220. These may include a display (e.g., monitor 210), a printer, a touch or force-feedback device, audio output devices, or the like.

Communications interface 290 can include hardware and/or software elements configured to provide unidirectional or bidirectional communication with other devices. For example, communications interface 290 may provide an interface between computer 220 and other communication networks and devices. Communications interface 290 may serve as an interface for receiving data from and transmitting data to other systems. Embodiments of communications interface 290 typically include an Ethernet card, a modem (telephone, satellite, cable, ISDN), (asynchronous) digital subscriber line (DSL) unit, FireWire interface, USB interface, and the like. For example, communications interface 290 may be coupled to a computer network, to a FireWire bus, or the like. In other embodiments, communications interface 290 may be physically integrated on the motherboard of computer 220, and may be a software program, such as soft DSL, or the like. In various embodiments, computer system 200 may also include software that enables communications over a network such as the HTTP, TCP/IP, RTP/RTSP protocols, and the like. In alternative embodiments of the present invention, other communications software and transfer protocols may also be used, for example IPX, UDP or the like.

FIG. 2 is representative of a computer system capable of embodying the present invention. It will be readily apparent to one of ordinary skill in the art that many other hardware and software configurations are suitable for use with the present invention. For example, the computer may be a desktop, portable, rack-mounted or tablet configuration. Additionally, the computer may be a series of networked computers. Further, the use of other micro processors are contemplated, such as Pentium™ or Itanium™ microprocessors; Opteron™ or AthlonXP™ microprocessors from Advanced Micro Devices, Inc; and the like. Further, other types of operating systems are contemplated, such as Windows®, WindowsXP®, WindowsNT®, or the like from Microsoft Corporation, Solaris from Sun Microsystems, LINUX, UNIX, and the like. In still other embodiments, the techniques described above may be implemented upon a chip or an auxiliary processing board.

Figure 3:
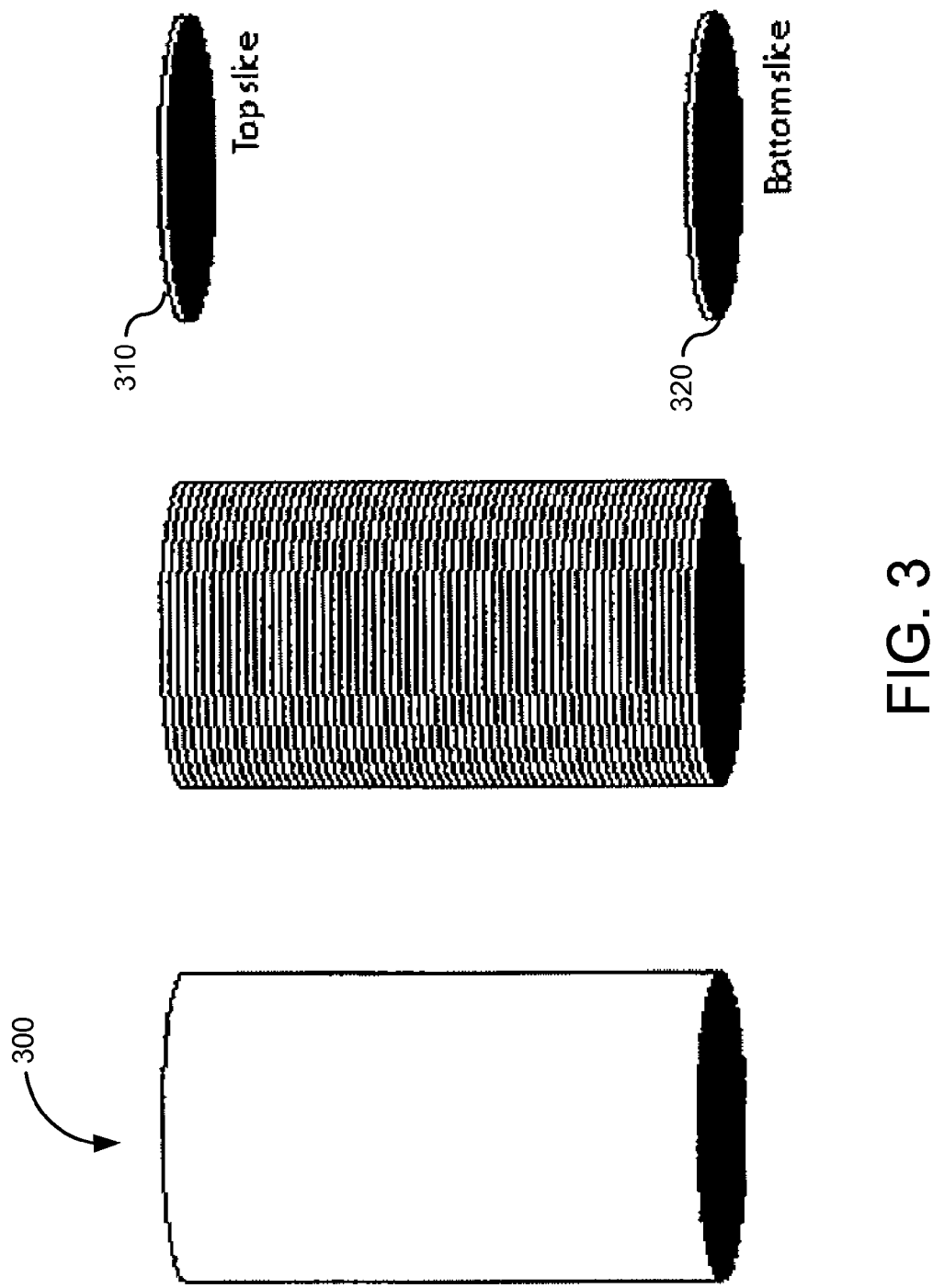
FIG. 3 is an illustration of information obtained using the medical imaging device of FIG. 1 that may be processed by the computer system or information processing device of FIG. 2 in various embodiments according to the present invention.

FIG. 3 is an illustration of information 300 obtained using medical imaging device 100 of FIG. 1 that may be processed by computer system 200 of FIG. 2 in various embodiments according to the present invention. Information 300 may be analyzed in order to extract critical high-temporal resolution physiological blood flow measurements.

One feature of CT compared with other imaging modalities is that the CT scanning process involves collecting raw projection data before reconstructing images. This collection of raw projection data is typically termed a "sinogram," because the data appear as a set of sinusoidal lines and bands. The sinusoidal structures can represent X-ray beam attenuation signals that are generated from X-ray generator assemblies 140, transmitted through all or part of a subject or other object, and received by X-ray detector assemblies 150, for example. A "sinogram image" may be displayed in a coordinate system determined by the positions of X-ray generator assemblies 150 and X-ray detector assemblies 150 for the X and Y coordinates, respectively.

Due to various image reconstruction techniques, a sinogram may contain information that is not available from its reconstructed image. For instance, a full CT scanning field of view is recorded in a sinogram, whereas a small subsection or region of interest of the full field of view is usually reconstructed in an image. At spiral CT, sinograms are acquired in a continuous fashion. With sinograms available, any transverse image can be specified for reconstruction at any longitudinal interval of scanning, which is particularly useful when overlapping images with a small reconstruction increment are needed to improve resolution.

Accordingly, while the temporal resolution of some types of information, such as CT images, obtained from medical imaging devices may be limited, sinograms in information 300 may offer sub-millisecond temporal resolution. For example, information 300 may include 700 or more projection datasets acquired per revolution by medical imaging device 100.

In one example, computed tomography angiography (CTA) provides a computed tomography technique that can be used to visualize specific arterial and venous vessels throughout a body. This ranges from arteries serving the brain to those bringing blood to the lungs, kidneys, arms and legs. CTA scans may be performed simultaneously with a high-speed injection of contrast material. A contrast material may include a liquid medium that can be injected into a vein, such as a small peripheral vein, using a needle or cannula. When the bulk of the contrast material (otherwise known as the "bolus") reaches the specific vessel or vessels of interest, a CTA scan may be triggered. Because the contrast material has been selected for its ability to attenuate X-rays more strongly than tissue surrounding the vessel or vessels of interest, the contrast material can be better visible in any resulting CT images. Using the bolus timing method, speed and shape of an incoming contrast bolus may be tracked using medical imaging device 100. By detecting the incoming contrast bolus at an upstream detector row, the progress of the contrast bolus may be tracked across all or part of a set of detector rows along a scan axis to a last downstream detector row. In various embodiments, information 300 including projection data acquired during a CT scan, rather than images reconstructed from the data, may be used to generate information about blood flow dynamics.

As a result, temporal resolution of raw projection data rises to about a factor of 1000 compared to image-based dynamic techniques, and thus enables more precise measurement of blood flow, for example, in narrow passages of fast-flowing vessels. While some dynamic aspects may be captured with alternate imaging modalities, such as MRIs and Ultrasound, these may not offer the spatial resolution and ease of use, for example of CT. Therefore, in some embodiments, blood flow dynamics using CT can vastly increase the ease of use, patient comfort, and attractiveness for many applications where otherwise costly and sometimes invasive exams may be required.

In some attempts, blood flow velocity is obtained using digital subtraction angiography. Great vessel blood flow (such as for the aorta, iliac vessels, superficial femoral, carotid) usually is evaluated in a rough fashion by injecting a small bolus of intravenous contrast, then by obtaining dynamic contrast enhanced CT images at two distant locations in the body (for example, at the upper abdominal aorta and then at the popliteal artery). The difference in the time to peak enhancement of the blood vessel between the two locations, divided by the distance between the two locations, can provide a rough estimate of mean blood flow velocity between the two locations.

However, this method is limited in that it requires two separate contrast bolus injections, and hence two separate dynamic contrast-enhanced CT scan series, one for each location. The requirement for two separate injections also introduces uncertainty regarding whether blood flow velocity changed during the time interval between the two injections. For example, if the blood flow velocity increased between the time of the first (proximal location) and second (distal location) scan acquisitions, then the calculated blood flow velocity would be much faster than the actual mean blood velocity, and could even be miscalculated as reversed flow velocity.

Figure 4:
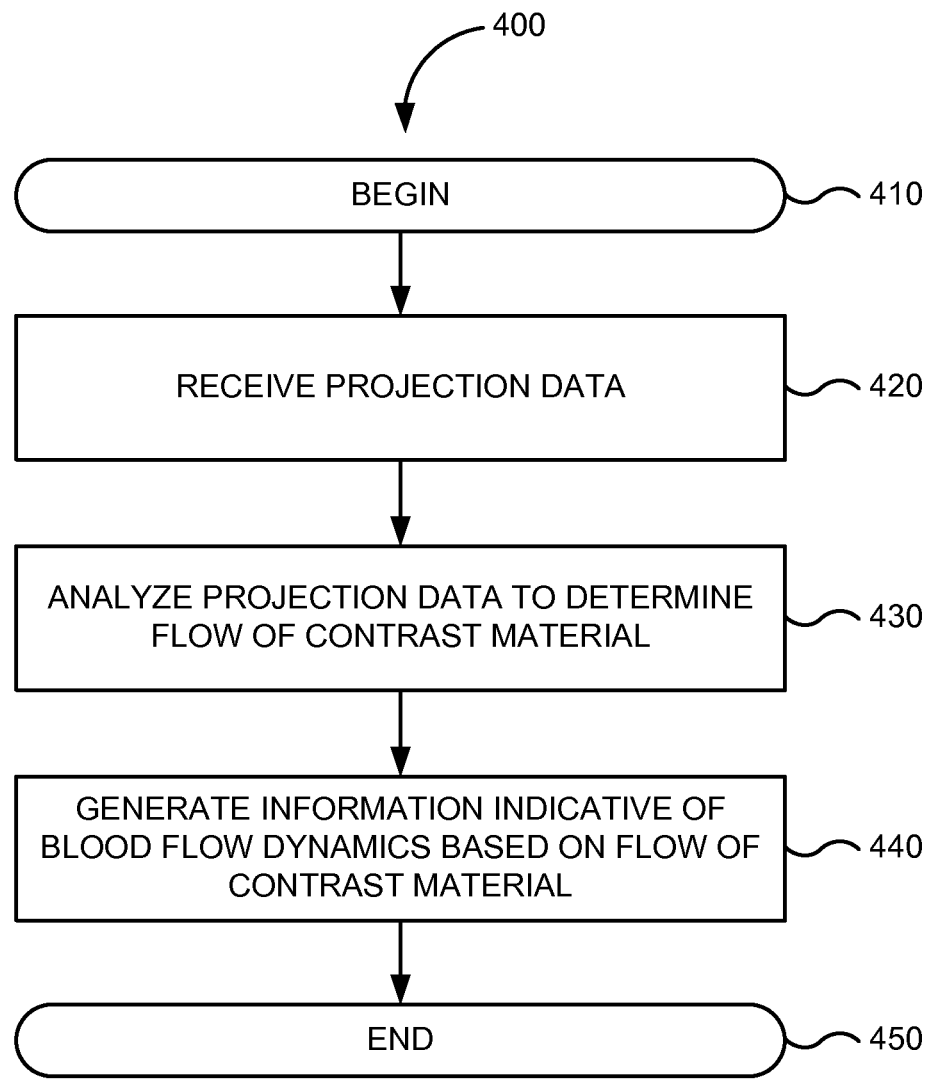
FIG. 4 is a simplified flowchart of a method for measuring blood flow dynamics in one embodiment according to the present invention.

FIG. 4 is a simplified flowchart of method 400 for measuring blood flow dynamics in one embodiment according to the present invention. The processing of method 400 depicted in FIG. 4 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 400 depicted in FIG. 4 begins in step 410.

In step 420, projection data is received. For example, one or more scans may be performed using medical imaging device 100 of FIG. 1 to generate the projection data. The projection data may include projection measurements from a multitude of angular positions, or views, from X-ray beam attenuation signals that are generated from X-ray generator assemblies 140, transmitted through all or part of a subject or other object being scanned, and received by X-ray detector assemblies 150. The projection data maybe received in real time, for example by information processing device 180, or retrieved from one or more storage devices where it was stored for offline processing. In various embodiments, medical imaging device 100 may collect raw projection data in the form of sinusoidal structures that represent X-ray beam attenuation signals that are generated from X-ray generator assemblies 140, transmitted through all or part of a subject or other object, and received by X-ray detector assemblies 150.

In step 430, the projection data is analyzed to determine flow (e.g., inflow) of a contrast material. For example, changes over time due to inflow of contrast material-enhanced blood may be determined. In one embodiment, each individual X-ray absorption data may be deconstructed to assess changes between projections due to inflow of the contrast material.

In step 440, information indicative of blood flow dynamics is generated based on the flow of the contrast material. Some examples of information that may be generated can include the speed (i.e., velocity) and shape (i.e., volume) of an incoming contrast bolus, pressure, turbulence, or the like. FIG. 4 end in step 450.

Figure 5:
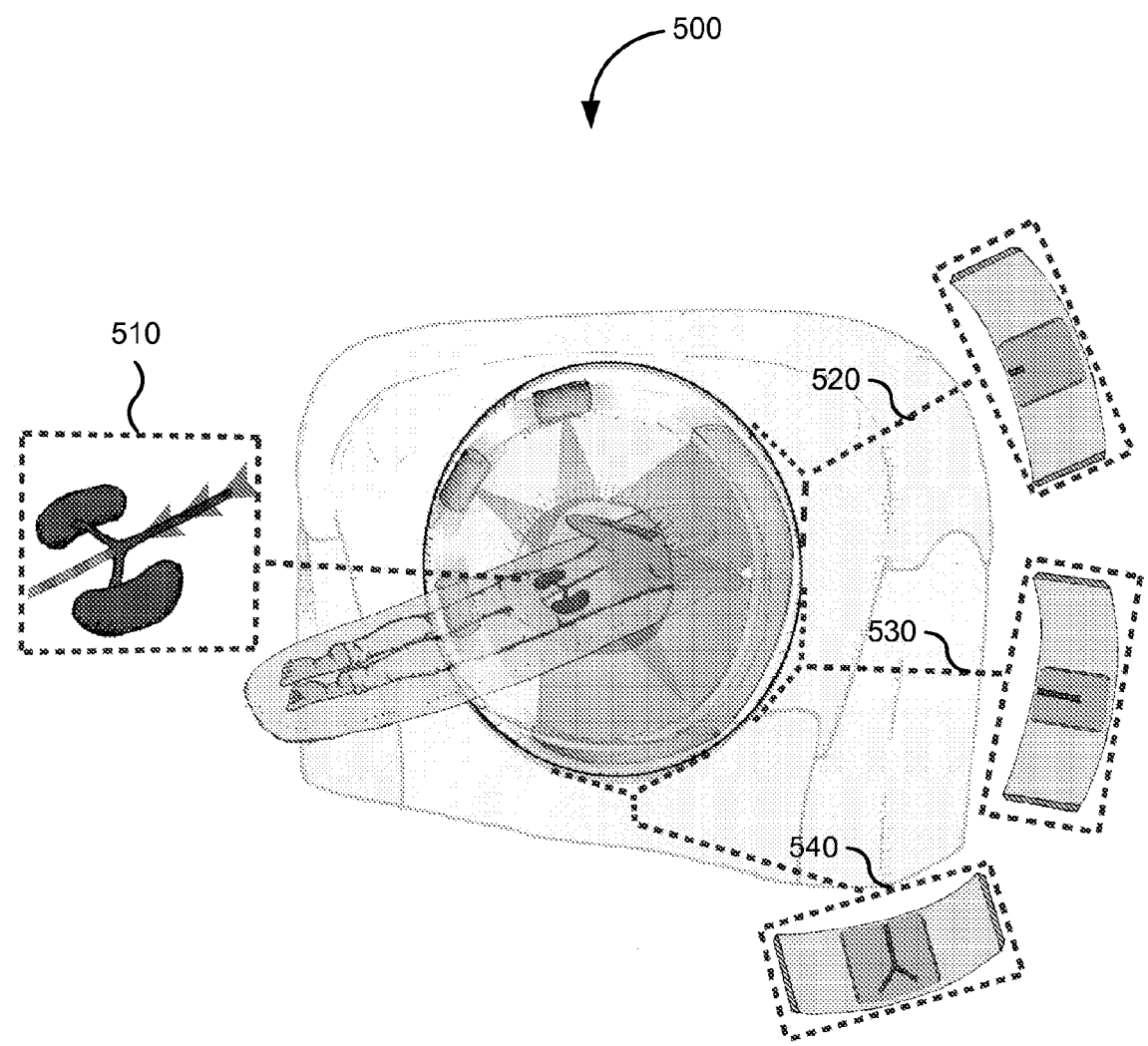
FIG. 5 is an illustration of a CT scanner in one embodiment that may be used to obtain measurements of blood flow dynamics in a subject.

FIG. 5 is an illustration of CT scanner 500 in one embodiment that may be used to obtain measurements of blood flow dynamics in a subject. In various embodiments, flow speed of a contrast agent can be quantifiable using raw projection data acquired by CT scanner 500. In one example, CT scanner 500 may collect about 1000 raw projections per typical reconstructed image. Therefore, a temporal resolution gain in flow speed measurement on the same order may be possible when compared to image based flow speed measurements. Projection data can be processed to determine the angular distance of projections with minimum square difference of relative contrast enhancement between detector rows.

Figure 6:
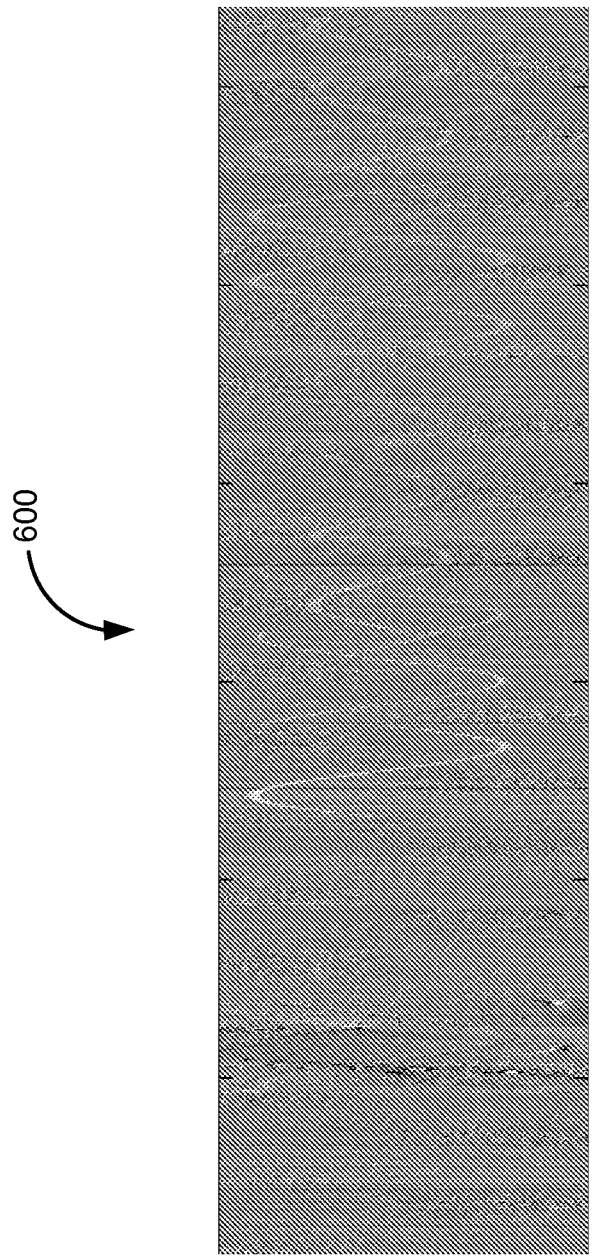
FIG. 6 depicts a sinogram that may be obtained from the CT scanner of FIG. 5 in one embodiment.

FIG. 6 depicts sinogram 600 that may be obtained from CT scanner 500 of FIG. 5 in one embodiment. In one embodiment, an incoming contrast bolus may be detected at an upstream detector row of CT scanner 500. Its progress may be followed across each of the detector rows down to the last downstream detector row. Assuming the shape of the contrast bolus does not significantly change while it crosses the distance covered by the detector rows, flow velocity of the contrast media can be determined.

In one example, a section of projection data acquired before contrast inflow can be extracted from acquired projection data (e.g., sinogram 600). A reference sinogram can then be subtracted from data acquired during contrast inflow to subtract background. This substation thereby can expose a contrast-only sinusoidal trace or traces of the contrast-filled vessel or vessels. Identification of the vessel of interest can then be executed either directly in the data or in reconstructed CT images. In the latter case, the identified regions containing the vessel of interest can be reprojected using the CT scanner geometry. The reprojection can coincide with the sinusoidal trace of the vessel. Changes of attenuation along this trace may be compared across detector rows. The angular or, equivalently, temporal offset between these changes can be computed. Division of the spatial distance between the detector rows and the temporal offset between their traces can used to determine blood flow dynamics.

Figure 7:
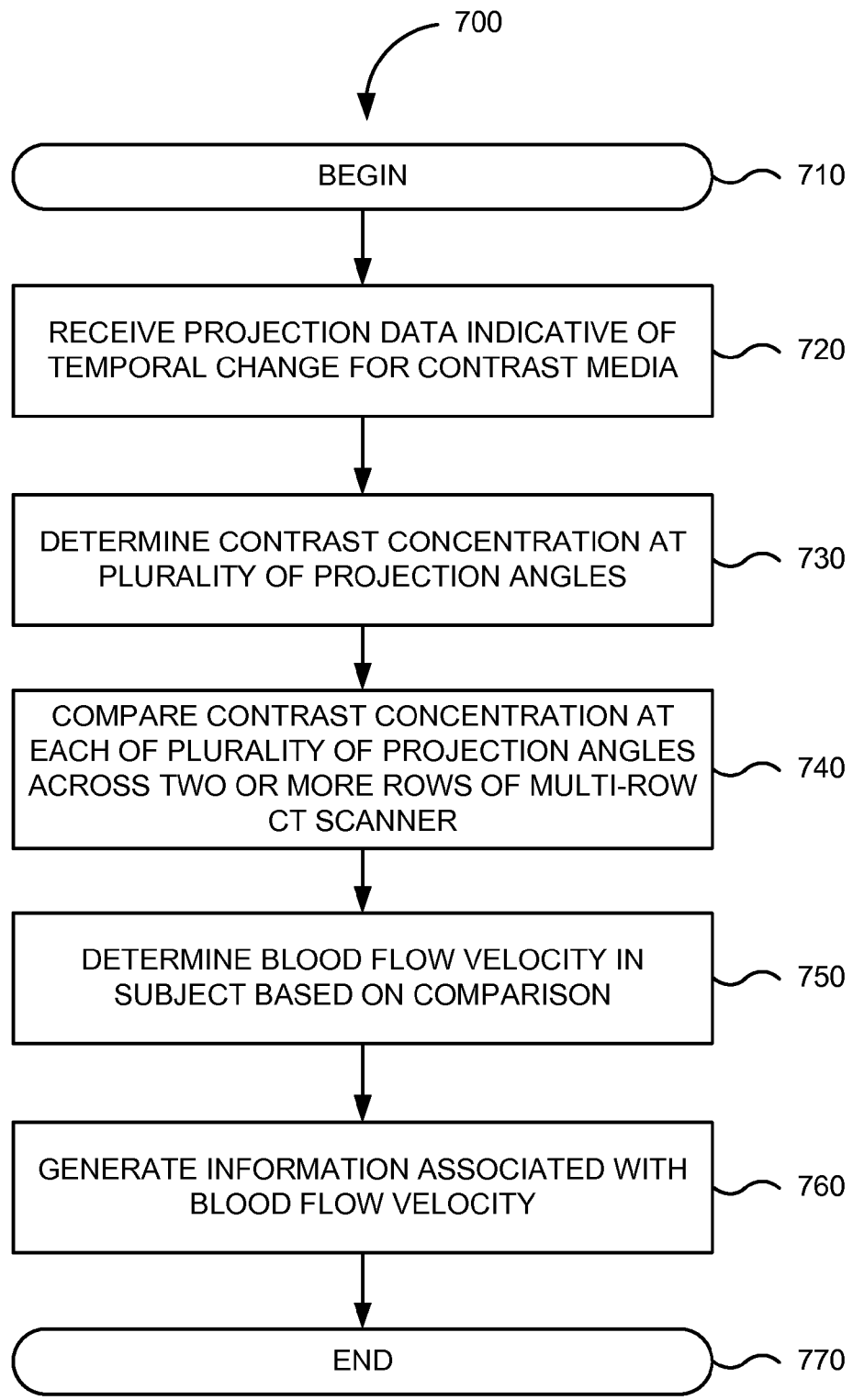
FIG. 7 is a flowchart of a method for measuring blood flow velocity in one embodiment according to the present invention.

FIG. 7 is a flowchart of method 700 for measuring blood flow velocity in one embodiment according to the present invention. The processing of method 700 depicted in FIG. 7 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 700 depicted in FIG. 7 begins in step 710.

In step 720, projection data is received. For example, the projection data may be received at an information processing device from a multi-row CT scanner. The projection data can be indicative of a temporal change for a contrast media, such as a change in the inflow a contrast media through arteries of a subject. In various embodiments, one or more pre-processing techniques may be performed on the projection data. For example, a section of projection data acquired before contrast inflow may be identified as a reference sinogram. The projection data may be processed using the reference sinogram to subtract reference elements, such as backgrounds or other artifacts. In one embodiment, such processing exposes a contrast-only sinusoidal trace in the projection data.

In step 730, a contrast concentration at each of a plurality of projection angles is determined. A contrast concentration may include a maximum color (e.g., grey) or intensity value at each of the plurality of projection angles. In various embodiments, the contrast-only sinusoidal trace in the projection data may be segmented and separated per detector row of the multi-row CT scanner. For example, for each row n, n=1, ... 16, the maximum grey value $p_{\theta_i, n}^{max}$ may be determined at each rotation angle $\theta_i = i\Delta\theta, i=1, \ldots, M$ where $\Delta\theta$ is the angular increment between projections and M is the number of projections per rotation.

In step 740, a contrast concentration at each of the plurality of projection angles is compared across at least two rows of the multi-row CT scanner. In some embodiments, a square difference is determined between two arbitrary detector rows n and m as a function of the angular difference:

$$SQ(j) = \sum_i \left(p_{\theta_i, n}^{max} - p_{\theta_{i+j}, m}^{max}\right)^2, j = 1, \ldots, M$$

In some embodiments, a smoothing may be performed by a convolution with a Gaussian kernel h. The angular difference may then be determined minimizing the filtered signal where:

$$j_{min} = \min_j (SQ(j) * h(j))$$

Because a projection angle can be a linear function of time elapsed since scan start, finding $j_{min}$ can be tantamount to finding the elapsed time for advancement of a contrast trace from its occurrence at detector row n to its occurrence at row m. Accordingly, this should also make clear the requirement of insignificant changes of the shape of the contrast bolus during its passage through any spatial section covered by a scan.

In step 750, blood flow velocity is determined based on the comparison between the contrast concentration at each of the plurality of projection angles across at least two rows of the multi-row CT scanner. For example, the flow velocity v may be determined as:

$$v = \frac{|m - n| \cdot \Delta d}{j_{min} \cdot T / M}$$

where $\Delta d$ represents the distance between two adjacent detector rows and T represents the duration of a full gantry rotation.

In step 760, information associated with blood flow velocity is generated. In various embodiments, the flow velocity v may be output or displayed to a user. Other elements, components, or factors used in determining blood flow velocity or derived there from may also be included in one or more reports, logs, user interfaces, or the like. FIG. 7 ends in step 770

Figure 8:
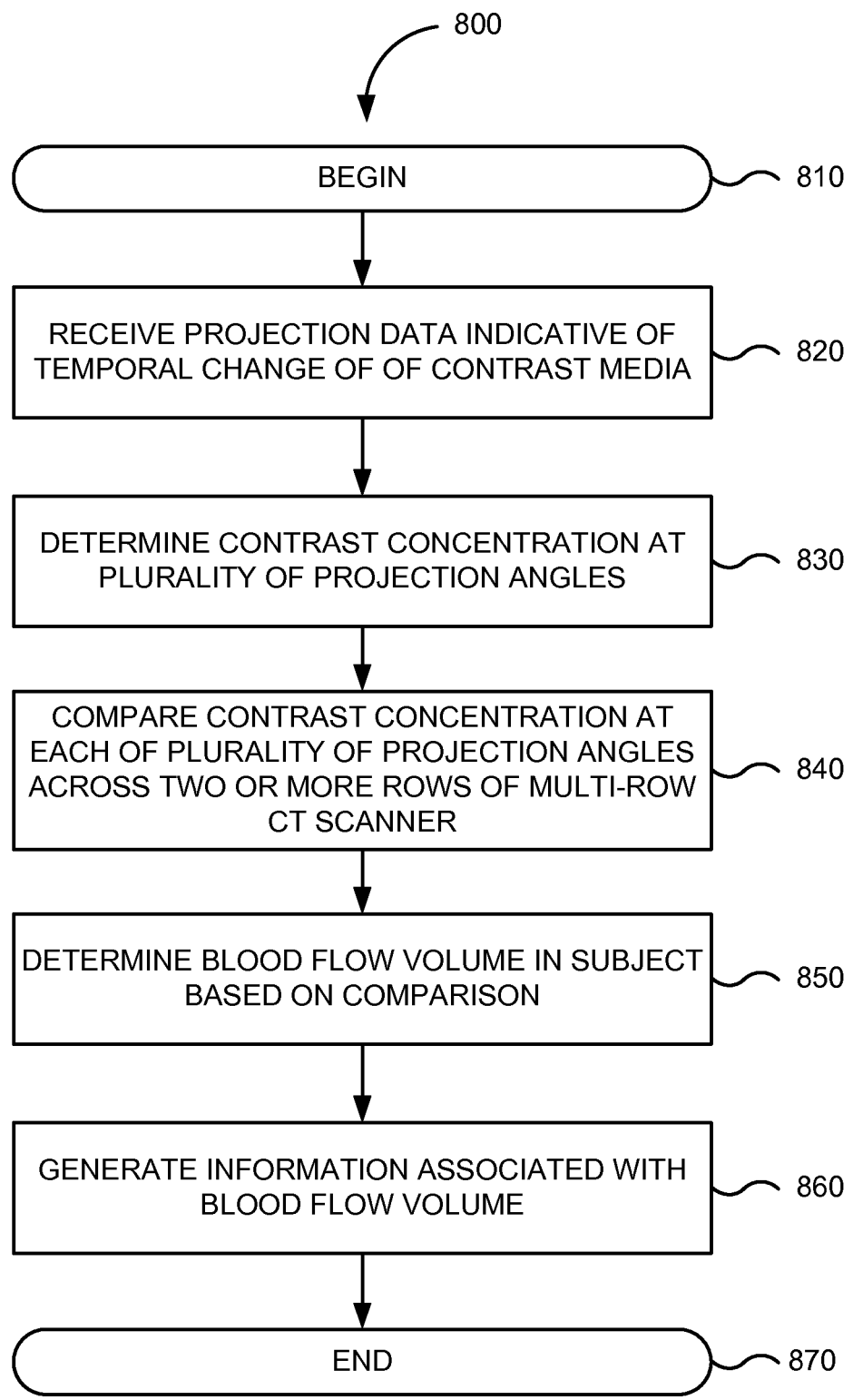
FIG. 8 is a flowchart of a method for measuring blood flow volume in one embodiment according to the present invention.

FIG. 8 is a flowchart of method 800 for measuring blood flow volume in one embodiment according to the present invention. The processing of method 800 depicted in FIG. 8 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 800 depicted in FIG. 8 begins in step 810.

In step 820, projection data is received. As discussed above, the projection data can be indicative of a temporal change for a contrast media, such as a change in the inflow a contrast media through arteries of a subject. In step 830, a contrast concentration at each of a plurality of projection angles is determined. In step 840, a contrast concentration at each of the plurality of projection angles is compared across at least two rows of the multi-row CT scanner.

In step 850, blood flow volume is determined based on the comparison between the contrast concentration at each of the plurality of projection angles across at least two rows of the multi-row CT scanner. For example, the flow volume V may be determined as:

$$V = v \times a$$

where v is velocity, determined in the same manner as in step 750, and a is the cross-sectional area of the blood vessel. a is easily determined using the reconstructed image segmentation information from step 830 and pixel dimensions:

$$a = [\text{pixel\_area}] \times [\text{inner\_vessel\_area\_in\_pixels}]$$

In step 860, information associated with blood flow volume is generated. In various embodiments, the flow volume V may be output or displayed to a user. Other elements, components, or factors used in determining blood flow volume or derived there from may also be included in one or more reports, logs, user interfaces, or the like. FIG. 8 ends in step 870.

Figure 9:
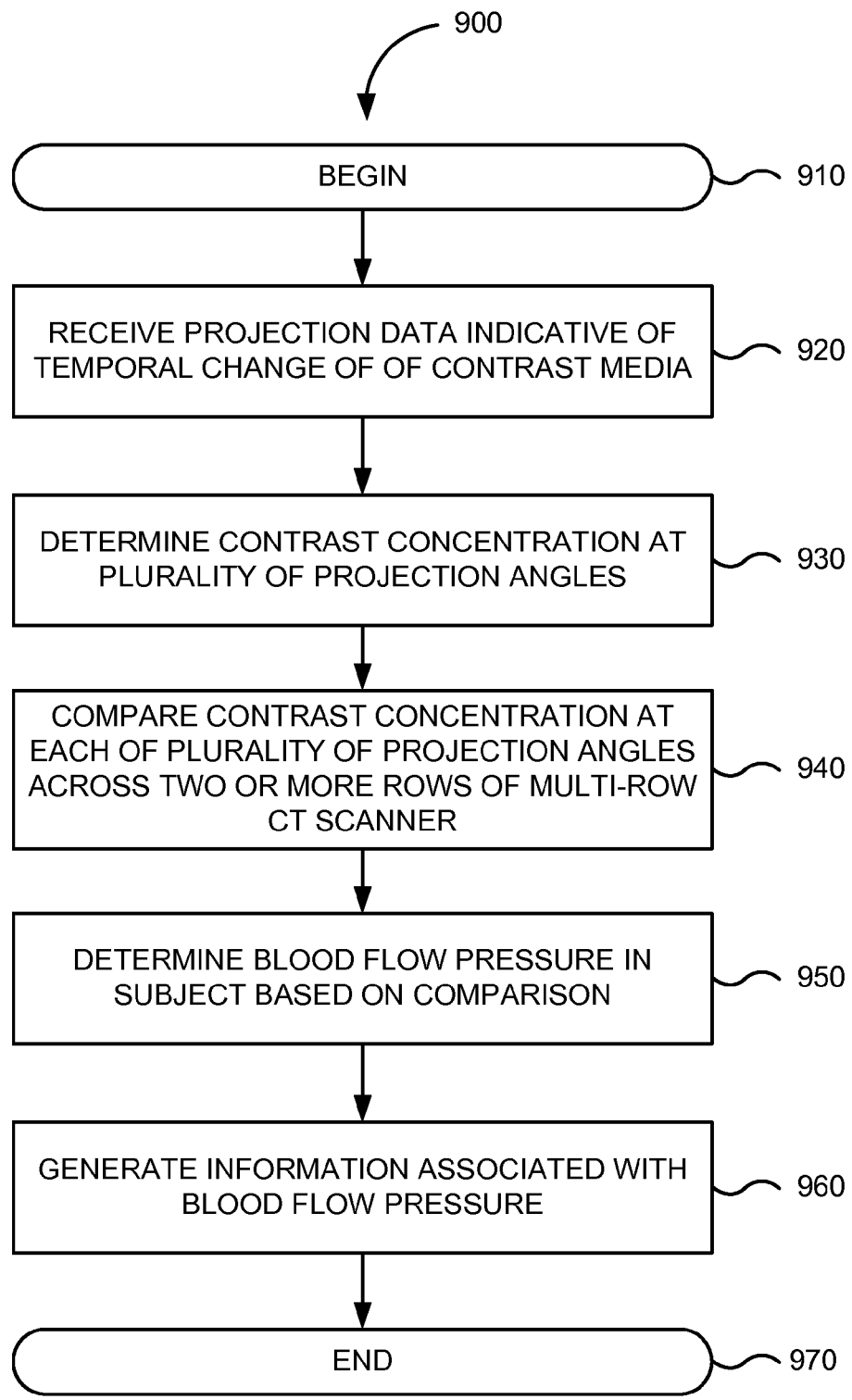
FIG. 9 is a flowchart of a method for measuring blood flow pressure in one embodiment according to the present invention.

FIG. 9 is a flowchart of method 900 for measuring blood flow pressure in one embodiment according to the present invention. The processing of method 900 depicted in FIG. 9 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 900 depicted in FIG. 9 begins in step 910.

In step 920, projection data is received. As discussed above, the projection data can be indicative of a temporal change for a contrast media, such as a change in the inflow a contrast media through arteries of a subject. In step 930, a contrast concentration at each of a plurality of projection angles is determined. In step 940, a contrast concentration at each of the plurality of projection angles is compared across at least two rows of the multi-row CT scanner.

In step 950, blood flow pressure is determined based on the comparison between the contrast concentration at each of the plurality of projection angles across at least two rows of the multi-row CT scanner. For example, an arterial blood pressure variation, ΔP, may be determined as:

$$\Delta P = P_2 - P_1 = \frac{1}{2} \rho_{blood} (v_1^2 - v_2^2)$$

Where ΔP represents the difference in pressure between two connected points within an artery. By measuring the velocities at two connected points within a blood vessel, say within a stenosis and a point surrounding it, one can derive the variation in blood pressure at the site of the stenosis. $\rho_{blood}$ represents the mass density of blood and $v_1$ and $v_2$ are to be measured using the techniques described in step 750.

In step 960, information associated with blood flow pressure is generated. In various embodiments, the arterial blood pressure variation, ΔP, may be output or displayed to a user. Other elements, components, or factors used in determining blood flow pressure or derived there from may also be included in one or more reports, logs, user interfaces, or the like. FIG. 9 ends in step 970.

Figure 10:
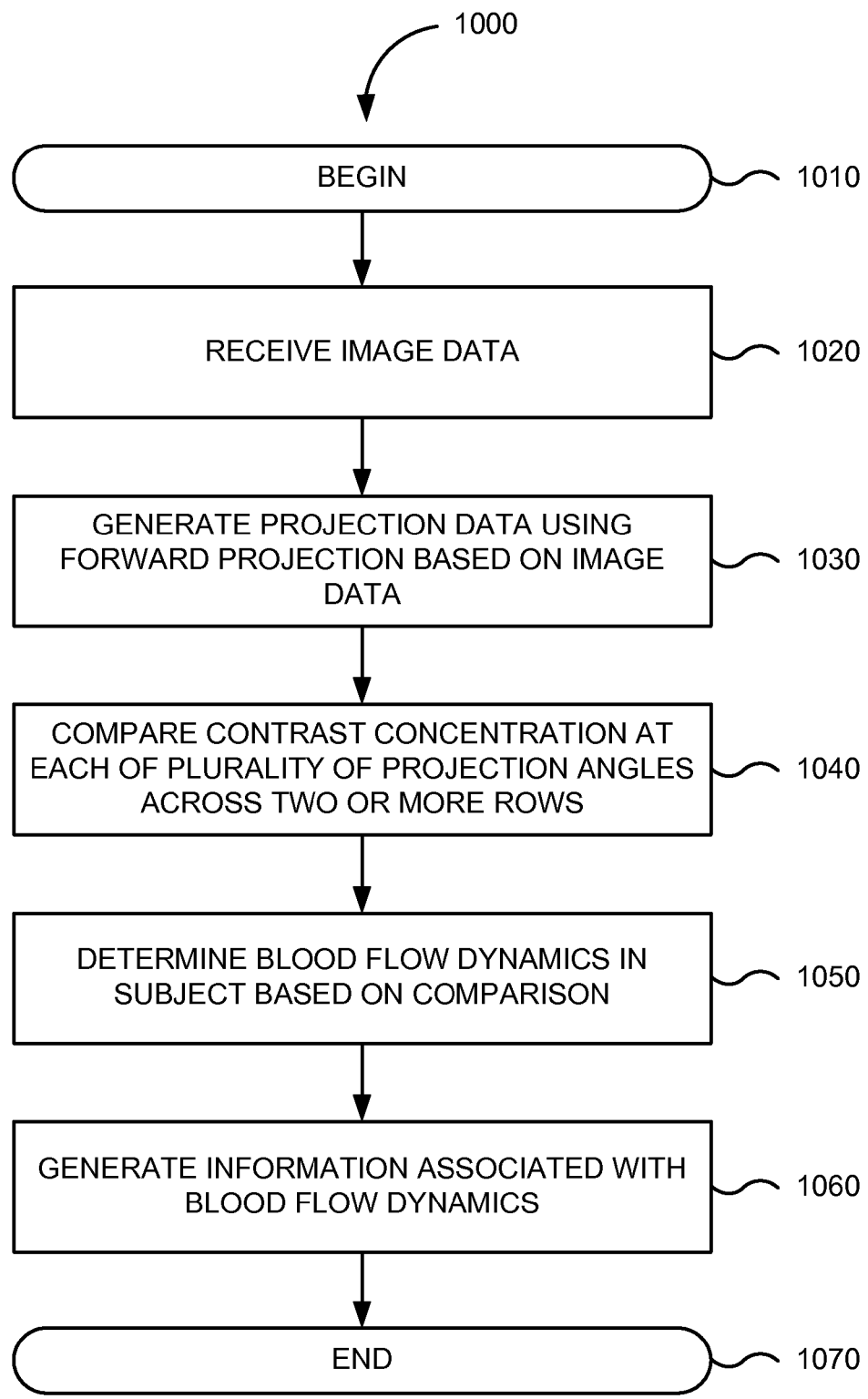
FIG. 10 is a flowchart of a method for measuring blood flow dynamics using a forward projection in one embodiment according to the present invention.

FIG. 10 is a flowchart of method 1000 for measuring blood flow dynamics using a forward projection in one embodiment according to the present invention. The processing of method 1000 depicted in FIG. 10 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 1000 depicted in FIG. 10 begins in step 1010.

In step 1020, image data is received. The image data may include stacks or sets of 3-D images taken by a CT scanner. In step 1030, projection data is generated using a forward protection based on the image data.

In step 1040, a contrast concentration at each of a plurality of projection angles is compared across at least two rows of a multi-row CT scanner. In step 1050, blood flow dynamics (e.g., velocity, volume, pressure, etc.) are determined based on the comparison between the contrast concentration at each of the plurality of projection angles across at least two rows of the multi-row CT scanner. In step 1060, information associated with blood flow dynamics is generated. FIG. 10 ends in step 1070.

Figure 11:
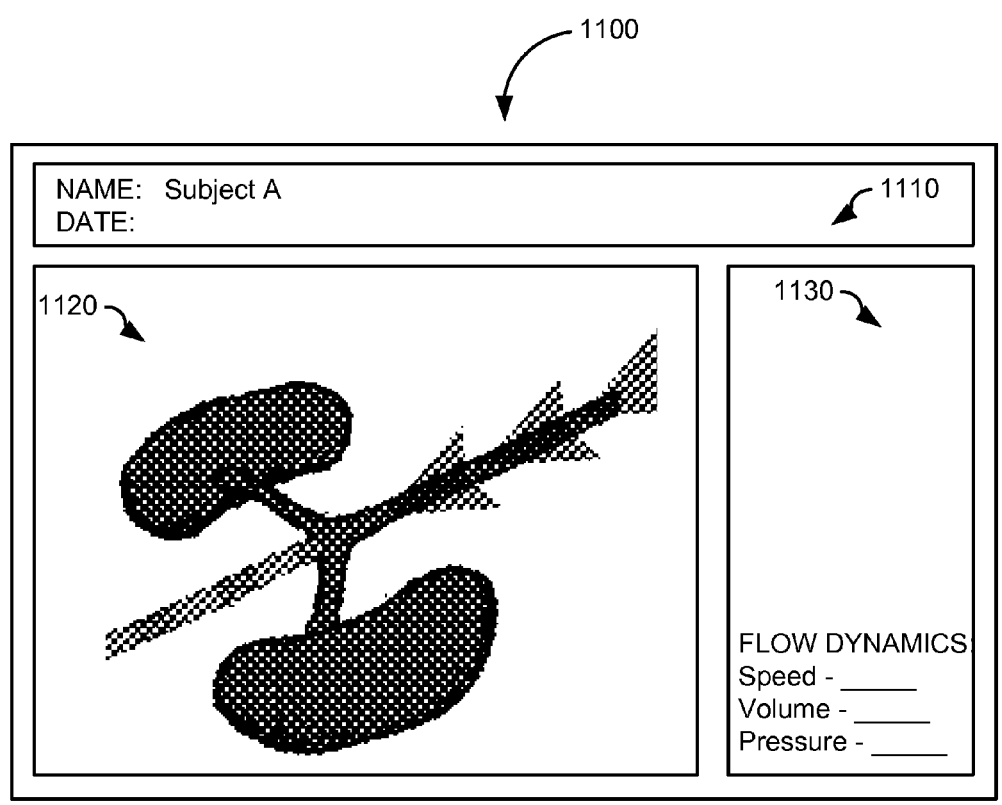
FIG. 11 is an illustration of a graphical user interface configured to display blood flow dynamics using the medical imaging device of FIG. 1 or the computer system or information processing device of FIG. 2 in various embodiments according to the present invention.

FIG. 11 is an illustration of graphical user interface (GUI) 1100 configured to display blood flow dynamics using medical imaging device 100 of FIG. 1 or computer system 200 of FIG. 2 in various embodiments according to the present invention. In this example, GUI 1100 includes panels or frames 1110, 1120, and 1130. Panel 1110 can include information associated with a scanning subject, such as name of subject, date of scan, medical records information, technical information, or the like.

Panel 1120 may include one or more n-dimensional representations of information. In some embodiments, panel 1120 may display 2-D or 3-D representations of subject anatomy. In further embodiments, panel 1120 may include animations or motion picture sequences illustrating patient anatomy, patient physiology, motion of contrast-enhanced blood or other medical devices introduced into the subject, information relayed from medical devices introduced into the subject, or the like. In this example, panel 1120 displays 3-D images of a patient's anatomy in combination with animations or other visual representations of blood flow dynamics, such as arrows whose direction may visually indicate blood flow direction, whose relative distance may visually indicated speed, whose sizes may visually indicate blood flow volume, pressure, or the like.

Panel 1130 may include one or more textual representations of information. In some embodiments, panel 1130 may display textual representations of subject anatomy, subject physiology, subject medical information, subject or equipment technical information, or the like. In this example, panel 1130 includes textual representations of blood flow dynamics, such as speed, volume, pressure, or the like.

Accordingly, GUI 1100 and other similarly configured interfaces may enable technicians, radiologists, doctors, clinicians, or the like to perform diagnostics in real-time while observing both patient anatomy and patient physiology.

Various embodiments of any of one or more inventions whose teachings may be presented within this disclosure can be implemented in the form of logic in software, firmware, hardware, or a combination thereof. The logic may be stored in or on a machine-accessible memory, a machine-readable article, a tangible computer-readable medium, a computer-readable storage medium, or other computer/machine-readable media as a set of instructions adapted to direct a central processing unit (CPU or processor) of a logic machine to perform a set of steps that may be disclosed in various embodiments of an invention presented within this disclosure. The logic may form part of a software program or computer program product as code modules become operational with a processor of a computer system or an information-processing device when executed to perform a method or process in various embodiments of an invention presented within this disclosure. Based on this disclosure and the teachings provided herein, a person of ordinary skill in the art will appreciate other ways, variations, modifications, alternatives, and/or methods for implementing in software, firmware, hardware, or combinations thereof any of the disclosed operations or functionalities of various embodiments of one or more of the presented inventions.

The disclosed examples, implementations, and various embodiments of any one of those inventions whose teachings may be presented within this disclosure are merely illustrative to convey with reasonable clarity to those skilled in the art the teachings of this disclosure. As these implementations and embodiments may be described with reference to exemplary illustrations or specific figures, various modifications or adaptations of the methods and/or specific structures described can become apparent to those skilled in the art. All such modifications, adaptations, or variations that rely upon this disclosure and these teachings found herein, and through which the teachings have advanced the art, are to be considered within the scope of the one or more inventions whose teachings may be presented within this disclosure. Hence, the present descriptions and drawings should not be considered in a limiting sense, as it is understood that an invention presented within a disclosure is in no way limited to those embodiments specifically illustrated.

Accordingly, the above description and any accompanying drawings, illustrations, and figures are intended to be illustrative but not restrictive. The scope of any invention presented within this disclosure should, therefore, be determined not with simple reference to the above description and those embodiments shown in the figures, but instead should be determined with reference to the pending claims along with their full scope or equivalents.

What is claimed is:

1. A method performed by an information processing device for measuring blood flow dynamics in a subject, the method comprising:
    receiving, at the information processing device, at least one set of sinogram data from a section of a revolution of a multi-row CT scanner indicative of a temporal change associated with flow of a contrast medium in the subject;
    determining a contrast concentration with the information processing device at each of a plurality of projection angles based on the sinogram data;
    determining blood flow velocity in the subject using the information processing device based on comparing the contrast concentration at each of the plurality of projection angles across two or more rows of the multi-row CT scanner; and
    generating information with the information processing device associated with the blood flow velocity of the subject.

2. The method of claim 1 wherein determining the contrast concentration with the information processing device at each of the plurality of projection angles comprises:
    determining a portion of the sinogram data representing data acquired before inflow of the contrast material.

3. The method of claim 1 wherein determining the contrast concentration with the information processing device at each of the plurality of projection angles comprises determining a maximum grey value at each of the plurality of projection angles.

4. The method of claim 1 wherein generating information with the information processing device associated with blood flow based on the comparing of the contrast concentration comprises generating information indicative of blood flow volume.

5. The method of claim 1 wherein generating information with the information processing device associated with blood flow based on the comparing of the contrast concentration comprises generating information indicative of pressure associated with the blood flow.

6. The method of claim 1 wherein determining the contrast concentration with the information processing device at each of the plurality of projection angles based on the sinogram data comprises:
    generating a contrast-only sinusoidal trace in response to subtracting a reference sinogram acquired before inflow of the contrast medium from one or more sinograms acquired during inflow of the contrast medium at least one of the plurality of projection angles.

7. The method of claim 1 wherein comparing the contrast concentration at each of the plurality of projection angles across one or more rows of the multi-row CT scanner using the information processing device comprises:
    determining a correlation between the contrast concentration at each projection angle and at least one of rows; and
    calculating a square difference of the contrast concentration of a first row and of the contrast concentration of a second row.

8. The method of claim 1 further comprising:
    displaying a value associated with speed of the blood flow on a display device based on the information.

9. The method of claim 1 further comprising:
    generating a set of images with the information processing device depicting a portion of the anatomy of the subject that was the focus of the one or more CT scans and a visual representation of the information associated with the blood flow.

10. The method of claim 1 further comprising:
    generating the sinogram data using a forward projection technique based on one or more 3-dimensional datasets.

11. A non-transitory computer-readable storage medium configured to store computer-executable code for measuring blood flow dynamics in a subject, the computer-readable storage medium comprising:
    code for receiving at least one set of sinogram data from a section of a revolution of a multi-row CT scanner indicative of a temporal change associated with flow of a contrast medium in the subject;
    code for determining a contrast concentration at each of a plurality of projection angles based on the sinogram data;
    code for determining blood flow velocity in the subject based on comparing the contrast concentration at each of the plurality of projection angles across two or more rows of the multi-row CT scanner; and
    code for generating information associated with the blood flow velocity of the subject.

12. The non-transitory computer-readable storage medium of claim 11 wherein the code for determining the contrast concentration with the information processing device at each of the plurality of projection angles comprises:
    code for determining a portion of the sinogram data representing data acquired before inflow of the contrast material.

13. The non-transitory computer-readable storage medium of claim 11 wherein the code for determining the contrast concentration with the information processing device at each of the plurality of projection angles comprises code for determining a maximum grey value at each of the plurality of projection angles.

14. The non-transitory computer-readable storage medium of claim 11 wherein the code for generating information with the information processing device associated with blood flow based on the comparing of the contrast concentration comprises code for generating information indicative of blood flow volume.

15. The non-transitory computer-readable storage medium of claim 11 wherein the code for generating information with the information processing device associated with blood flow based on the comparing of the contrast concentration comprises code for generating information indicative of pressure associated with the blood flow.

16. The non-transitory computer-readable storage medium of claim 11 wherein the code for determining the contrast concentration with the information processing device at each of the plurality of projection angles based on the sinogram data comprises:
    code for generating a contrast-only sinusoidal trace in response to subtracting a reference sinogram acquired before inflow of the contrast medium from one or more sinograms acquired during inflow of the contrast medium at least one of the plurality of projection angles.

17. The non-transitory computer-readable storage medium of claim 11 wherein the code for comparing the contrast concentration at each of the plurality of projection angles across one or more rows of the multi-row CT scanner using the information processing device comprises:
    code for determining a correlation between the contrast concentration at each projection angle and at least one of rows; and
    code for calculating a square difference of the contrast concentration of a first row and of the contrast concentration of a second row.

18. The non-transitory computer-readable storage medium of claim 11 further comprising:
    code for displaying a value associated with speed of the blood flow on a display device based on the information.

19. The non-transitory computer-readable storage medium of claim 11 further comprising:
    code for generating a set of images with the information processing device depicting a portion of the anatomy of the subject that was the focus of the one or more CT scans and a visual representation of the information associated with the blood flow.

20. The non-transitory computer-readable storage medium of claim 11 further comprising:
    code for generating the sinogram data using a forward projection technique based on one or more 3-dimensional datasets.

21. An information processing device for measuring blood flow dynamics in a subject, the information processing device comprising:
    a processor; and
    a memory coupled to the processor and configured to store processor-executable instructions that configure the processor to:
        receive at least one set of sinogram data from a section of a revolution of a multi-row CT scanner indicative of a temporal change associated with flow of a contrast medium in the subject;
        determine a contrast concentration at each of a plurality of projection angles based on the sinogram data;
        determine blood flow velocity in the subject based on comparing the contrast concentration at each of the plurality of projection angles across two or more rows of the multi-row CT scanner; and
        generate information associated with the blood flow velocity of the subject.

22. The information processing device of claim 21 wherein the processor is configured to determine a portion of the sinogram data representing data acquired before inflow of the contrast material to determine the contrast concentration with the information processing device at each of the plurality of projection angles.

23. The information processing device of claim 21 wherein the processor is configured to determine a maximum grey value at each of the plurality of projection angles to determine the contrast concentration with the information processing device at each of the plurality of projection angles.

24. The information processing device of claim 21 wherein the processor is configured to generate information indicative of blood flow volume to generate information with the information processing device associated with blood flow based on the comparing of the contrast concentration.

25. The information processing device of claim 21 wherein the processor is configured to generate information indicative of pressure associated with the blood flow to generate information with the information processing device associated with blood flow based on the comparing of the contrast concentration.

26. The information processing device of claim 21 wherein the processor is configured to generate a contrast-only sinusoidal trace in response to subtracting a reference sinogram acquired before inflow of the contrast medium from one or more sinograms acquired during inflow of the contrast medium at least one of the plurality of projection angles to determine the contrast concentration with the information processing device at each of the plurality of projection angles based on the sinogram data.

27. The information processing device of claim 21 wherein the processor is further configured to compare the contrast concentration at each of the plurality of projection angles across one or more rows of the multi-row CT scanner using the information processing device by:
    determining a correlation between the contrast concentration at each projection angle and at least one of rows; and
    calculating a square difference of the contrast concentration of a first row and of the contrast concentration of a second row.

28. The information processing device of claim 21 wherein the processor is further configured to display a value associated with speed of the blood flow on a display device based on the information.

29. The information processing device of claim 21 wherein the processor is further configured to generate a set of images with the information processing device depicting a portion of the anatomy of the subject that was the focus of the one or more CT scans and a visual representation of the information associated with the blood flow.

30. The information processing device of claim 21 wherein the processor is further configured to generate the sinogram data using a forward projection technique based on one or more 3-dimensional datasets.

31. A system for measuring blood flow dynamics in a subject, the system comprising:
    means for receiving at least one set of sinogram data from a section of a revolution of a multi-row CT scanner indicative of a temporal change associated with flow of a contrast medium in the subject;

means for determining a contrast concentration at each of a plurality of projection angles based on the sinogram data;

means for determining blood flow velocity in the subject based on comparing the contrast concentration at each of the plurality of projection angles across two or more rows of the multi-row CT scanner; and means for generating information associated with the blood flow velocity of the subject.

* * * * *